United States Patent [19]

Takeda et al.

[11] Patent Number: 5,021,197
[45] Date of Patent: Jun. 4, 1991

[54] PROCESS FOR PRODUCTION OF SULFONIUM COMPOUNDS

[75] Inventors: Mutsuhiko Takeda; Masamichi Mizukami; Yasumasa Norisue; Isao Hagiwara; Fumiya Zaima, all of Tokyo, Japan

[73] Assignee: Mitsubishi Gas Chemical Company, Inc., Tokyo, Japan

[21] Appl. No.: 358,872

[22] Filed: May 26, 1989

[30] Foreign Application Priority Data

Jun. 16, 1988 [JP] Japan ................... 63-146901
Oct. 18, 1988 [JP] Japan ................... 63-260579
Jan. 31, 1989 [JP] Japan ................... 1-19780

[51] Int. Cl.$^5$ ............................... C08H 3/00
[52] U.S. Cl. .................. 260/399; 260/410.5; 560/142
[58] Field of Search ............ 560/142; 558/60; 544/158; 260/399, 410.5

[56] References Cited

U.S. PATENT DOCUMENTS 4,857,656 8/1989 Kauge ......................... 560/142

OTHER PUBLICATIONS

Kauge et al., Bull. of Chem. Soc. Jap., vol. 60, 1987, pp. 2409-2418.
In re Durden, 226 USPQ 359.

Primary Examiner—Jose G. Dees
Assistant Examiner—Deborah D. Carr
Attorney, Agent, or Firm—Frishauf, Holtz, Goodman & Woodward

[57] ABSTRACT

A process for producing a sulfonium compound of the formula (III)

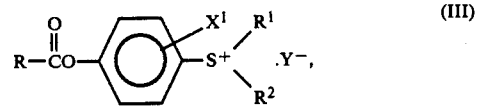

which process comprises reacting a p-dialkylsulfoniophenol of the formula (I)

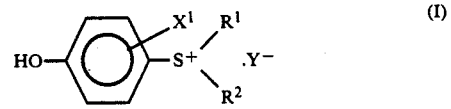

and a carbonyl halogenide compound of the formula (II)

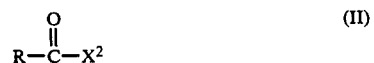

in the presence of a secondary amine having a structure in which two secondary alkyl groups are linked to the nitrogen atom, wherein $R^1$ and $R^2$ are the same or different and are independently an alkyl group having 1 to 4 carbon atoms, $X^1$ is a hydrogen atom, a halogen atom or an alkyl group having 1 to 4 carbon atoms, $Y^-$ is a halogen anion, a perchlorate anion, an alkylsulfate anion, a hydrogensulfate anion or a p-toluenesulfonate anion, R is an alkyl group having 1 to 20 carbon atoms, a tert-butoxy group, a benzyloxy group, a p-methoxybenzyloxy group, a phenyl group or a 9-fluorenylmethoxy group, and $X^2$ is a halogen atom, wherein the reacting is carried out in a solvent selected from the group consisting of polar aprotic solvents, ethers and halogenated hydrocarbons, at a temperature of −80° C. to 30° C. and for a reaction time of 0.5 hour to 10 hours.

26 Claims, No Drawings

PROCESS FOR PRODUCTION OF SULFONIUM COMPOUNDS

BACKGROUND OF THE INVENTION

1. Field of the Invention

The present invention relates to a process for the production of sulfonium compounds and more particularly to a process for producing acylated sulfonium compounds by acylating the phenolic hydroxyl group of p-dialkylsulfoniophenols having a specified structure, in the presence of specified secondary amines. The term "acyl" as used herein refers to a group as derived by removal of a hydroxyl group from a carboxylic acid or a carbonic acid monoester.

2. Description of the Related Arts

Sulfonium compounds represented by the general formula:

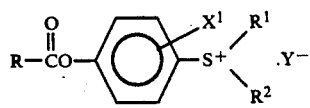

(wherein all the symbols are as defined hereinafter) are useful compounds for reagents for introduction of an acyl group as a protecting group in the organic chemical field, e.g., synthesis of peptides, because they exhibit acylating action in an aqueous solution.

For production of the sulfonium compounds represented by the above general formula, by acylating the phenolic hydroxyl group of p-dialkylsulfoniophenols, a method of reacting acid halides, i.e., carbonylhalogenide compounds in the presence of a base, has been generally employed. For example, Bull. Chem. Soc. Japan, 60 (7), 2409 to 2418 (1987) and Japanese Patent Application Laid-Open No. 8365/1988 disclose a method in which acid chloride is used as the acid halide, and a tertiary amine, e.g., triethylamine, as the base. In this method, not primary or secondary amines but tertiary amines are used as the base to prevent side reactions.

This method, however, is not necessarily satisfactory for practical use, because if in the acylation of the phenolic hydroxyl group of p-dialkylsulfoniophenols, the carbonylhalogenide compound and the above phenol compound are reacted in the presence of a base, e.g., a tertiary amine such as triethylamine, the yield of the desired acylated compound (sulfonium compound of the above general formula) is low, and the amine salt and by-products are not easy to separate.

For example, when p-dimethylsulfoniophenol methylsulfate and p-methoxybenzyloxycarbonyl chloride were reacted in the presence of triethylamine as the tertiary amine, the yield of the desired product, p-methoxybenzyl p-dimethylsulfoniophenyl carbonate methylsulfate, was as low as less than 30%. When N,N-dimethylaniline was used as the tertiary amine, the desired product could not be obtained at all.

When p-dimethylsulfoniophenol methylsulfate and 9-fluorenylmethoxycarbonyl chloride were reacted in the presence of triethylamine, the yield of the desired product, 9-fluorenylmethyl p-dimethylsulfoniophenyl carbonate

SUMMARY OF THE INVENTION

An object of the present invention is to provide a process for production of the aforementioned sulfonium compounds in high yields with almost no side reactions.

Another object of the present invention is to provide a process for production of the aforementioned sulfonium compounds, in which the sulfonium compounds can be easily isolated and purified, so that the sulfonium compounds can be obtained in high purity with high efficiency.

The present invention relates to a process for producing sulfonium compounds represented by the general formula (III) as described below which comprises reacting p-dialkylsulfoniophenols represented by the general formula (I) as described below and carbonyl halogenide represented by the general formula (II) as described below in the presence of a secondary amine having the structure in which two secondary alkyl groups are linked to the nitrogen atom.

General Formula (I)

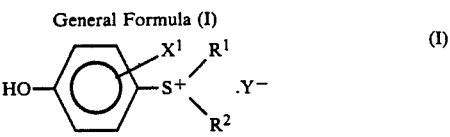

General Formula (II)

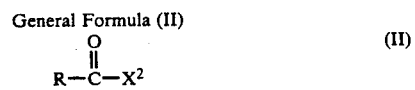

General Formula (III)

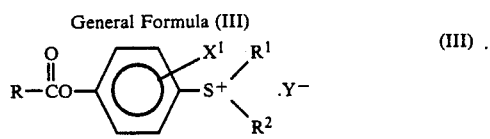

In the above general formulae (I) and (III), $R^1$ and $R^2$ may be the same or different and are independently an alkyl group having 1 to 4 carbon atoms, $X^1$ is a hydrogen atom, a halogen atom or an alkyl group having 1 to 4 carbon atoms, and $Y^-$ is a halogen anion, a perchlorate anion, an alkylsulfate anion, a hydrogensulfate anion or a p-toluenesulfonate anion.

In the above general formulae (II) and (III), R is an alkyl group having 1 to 20 carbon atoms, a tert-butoxy group, a benzyloxy group, a p-methoxybenzyloxy group, a phenyl group or a 9-fluorenylmethoxy group, and $X^2$ is a halogen atom, e.g., fluorine, chlorine or bromine.

DESCRIPTION OF PREFERRED EMBODIMENTS

In p-dialkylsulfoniophenol represented by the general formula (I) which is to be used as the starting material in the present invention, the alkyl group of $R^1$ or $R^2$ is preferably a lower alkyl group having 1 to 4 carbon atoms and more preferably a methyl group or an ethyl group. The anion $Y^-$ is a halogen anion, a perchlorate anion, an alkylsulfate anion, a hydrogensulfate anion or a p-toluenesulfonate anion. From the viewpoint of water solubility of the desired product, an alkylsulfate anion and a hydrogensulfate anion are preferred, and among the alkylsulfate anions, a methylsulfate anion is particularly preferred.

$X^1$ is appropriately chosen from a hydrogen atom, a halogen atom and an alkyl group depending on the solubility of the compound of the general formula (III), the acylating reactivity and so forth. Examples of the halogen atom are fluorine, chlorine and bromine. When $X^1$ is an alkyl group, a lower alkyl group having 1 to 4 carbon atoms is preferred.

The carbonyl halogenides (i.e., acid halides) as represented by the general formula (II) include acetyl fluoride, acetyl chloride, propionyl chloride, propionyl bromide, butyryl chloride, valeryl chloride, hexanoyl chloride, octanoyl chloride, decanoyl chloride, lauroyl chloride, myristoyl chloride, palmitoyl chloride, stearoyl chloride, tert-butoxycarbonyl chloride, benzyloxycarbonyl chloride, p-methoxybenzyloxycarbonyl chloride, 9-fluorenyl-methoxycarbonyl chloride, benzoyl chloride, and benzoyl bromide. Of these halides, chlorides are preferred from the viewpoints of stability and reactivity.

In the case where relatively unstable carbonyl halogenides, e.g., tert-butoxycarbonyl chloride or p-methoxybenzyloxycarbonyl chloride, are used, the process of the present invention is particularly apt to give excellent results compared with conventional processes.

One of the features of the present invention is that secondary amines having a specified structure (hereinafter sometimes referred to merely as "secondary amines") are used in reacting phenols of the general formula (I) and carbonyl halogenide of the general formula (II).

Secondary amines having the specified structure to be used in the present invention are secondary amines having the structure in which two secondary alkyl groups are linked to the nitrogen atom. Namely the term "secondary amine" as used herein includes alicyclic amines in which both α-carbon atoms (i.e., carbon atoms linked to the nitrogen atom) have side chain, respectively (e.g., 2,6-dimethylpiperidine).

The term "secondary alkyl group" as used herein includes a cyclic alkyl group. And the term "two secondary alkyl groups" includes an alkylene group in which the carbon chain is branched at both ends (i.e., positions at which the carbon chain is linked to the nitrogen atom).

Examples of the secondary amines to be used in the present invention are dicyclohexylamine, diisopropylamine, di-sec-butylamine, and 2,6-dimethylpiperidine.

In the process of the present invention, the secondary amine is used in an amount of 0.5 to 2.0 mol, preferably 0.8 to 1.5 mol per mol of the p-dialkylsulfoniophenol of the general formula (I). The carbonyl halogenide compound of the general formula (II) is also used in an amount of 0.5 to 2.0 mol, preferably 0.8 to 1.5 mol per mol of the p-dialkylsulfoniophenol of the general formula (I).

In the process of the present invention, the carbonyl halogenide is added to the reaction system while usually maintaining the reaction temperature at $-80$ to $+30°$ C. and preferably $-30$ to $+10°$ C. although the temperature varies depending on the type of the carbonyl halogenide. Some of the carbonyl halogenides decompose by increasing temperatures over 10° C. And usually increasing temperature tends to increase side reaction. On the other hand, maintaining the temperature at a level lower than $-80°$ C. is undesirable from an economic standpoint. For the reasons described above, the reaction should be carried out for 0.5 to 10 hours while maintaining the reaction temperature at $-80$ to $+30°$ C., and preferably $-30$ to $+10°$ C. When 9-fluorenyl-methoxycarbonyl chloride is used as the carbonyl halogenide of the general formula (II), it is suitable for the reaction to be carried out for about 0.5 to 4 hours at a temperature of $-20$ to $+30°$ C., preferably $-10$ to $20°$ C.

The reaction of the present invention is usually carried out in a solvent. Solvents which can be used include polar aprotic solvents, e.g., acetonitrile, ethers, e.g., diethyl ether or tetrahydrofuran, and halogenated hydrocarbons, e.g., dichloromethane. Of these solvents, acetonitrile is preferred.

In the present invention, there are no special limitations to the order in which the starting materials and the solvent are added; the compounds may be added simultaneously or successively. In any of the cases in which (1) a solution of carbonyl halogenide is added to a mixture of p-dialkylsulfoniophenol, secondary amine and a solvent, and (2) secondary amine is added to a mixture of p-dialkylsulfoniophenol, carbonyl halogenide and a solvent, the desired product can be obtained in a high yield. It is also possible that all the starting materials and the solvent are added and mixed almost simultaneously.

After completion of the reaction, the amine salt formed can be easily removed by filtration. The filtrate was concentrated under reduced pressure. The desired product, the sulfonium compound of the general formula (III), was crystallized by adding the polar solvent e.g., ethyl acetate or diethyl ether. If necessary, it is purified by recrystallization.

In accordance with the process of the present invention in which the secondary amines as specified above are used as the base, the desired sulfonium compounds can be obtained in high yields with almost no undesirable side reactions. Moreover, since the amine salt formed at the same time can be easily removed, the desired sulfonium compounds can be isolated and purified to a high purity by a simplified procedure.

Accordingly the process of the present invention is extremely useful for production of the sulfonium compounds represented by the general formula (III).

The present invention is described in greater detail with reference to the following examples. In a case where the purity of the sulfonium compound is not indicated, the purity as determined by the nuclear magnetic resonance (NMR) method was presumed to be more than 95%.

EXAMPLE 1

A separable flask provided with a glass filter at the bottom thereof so as to permit suction filtration, and jacketed to permit cooling was used as a reactor. In this flask, 7.41 g (0.1 mol) of tert-butyl alcohol and 150 ml of dried ether were placed and cooled to $-40°$ C., and then 13.2 ml (0.2 mol) of phosgene was introduced thereinto. Then a solution of 9.7 ml (0.12 mol) of pyridine in 40 ml of ether was dropped at $-40°$ C. over 30 minutes while stirring. After completion of the dropwise addition, the reaction temperature was raised to $-20°$ C., the reaction mixture was stirred for 2 hours and then allowed to stand at $-20°$ C. for 15 hours. This mixture is referred to as "Solution A".

Separately, 10.64 g (0.04 mol) of p-dimethylsulfoniophenol methylsulfate was dissolved in 200 ml of dried acetonitrile at 40° C., and 8.0 ml (0.04 mol) of dicyclohexylamine was added thereto. Then the resulted mixture was cooled in an ice bath. This mixture is referred to as "Solution B".

A hundred milliliters of a mixture of excessive phosgene and ether was removed from Solution A under reduced pressure at a temperature of not more than −20° C. to obtain a solution containing tert-butoxycarbonyl chloride. This solution was dropped into Solution B while filtering with the glass filter at the same temperature as above.

The solid material remaining on the glass filter was washed with 100 ml of ether which had been cooled to not more than −20° C. The washings were dropped through the glass filter in the same manner as above. The time required for these dropping and washing was 30 minutes.

This reaction mixture was stirred at 0° C. for 2 hours, and a white solid of amine hydrochloride was separated by filtration. The white solid was washed with 200 ml of acetonitrile. The filtrate obtained by the above filtration and the acetonitrile used for the above washing were mixed, and the resulted mixture was concentrated under reduced pressure.

Ethyl acetate was added to the concentrated solution. Then white crystal was precipitated. This crystal was collected by filtration and recrystallized from acetonitrile-ethyl acetate. This crystal was the desired sulfonium compound, tert-butyl p-dimethylsulfoniophenyl carbonate methylsulfate.

Yield: 4.62 g (12.6 mmol, 31.5%).
Melting Point: 118–121° C.
1H-NMR(CDCL3) $\delta = 1.54$, 9H(s); 3.43, 6H(s); 3.66, 3H(s); 7.39, 2H(d,J=10 Hz); 8.17, 2H(d,J=10 Hz).

COMPARATIVE EXAMPLE 1

The procedure of Example 1 was repeated with the exception that triethylamine was used in place of the dicyclohexylamine. Since the product contained a fair amount of impurities, it was purified by the use of a silica gel column (CHC13:CH3OH=9:1) and then again precipitated with acetonitrile-ether to obtain 0.36 g (0.98 mmol) of the desired product, tert-butyl p-dimethylsulfoniophenyl carbonate methylsulfate (yield 2.5%).

EXAMPLE 2

Eight point zero grams (30 mmol) of p-dimethyl-sulfoniophenol methylsulfate was added to 200 ml of dried acetonitrile and then stirred at room temperature for 30 minutes. Six point zero grams (33 mmol) of dicyclohexylamine was added, and the resulting mixture was stirred at room temperature for 1 hour and then cooled to 0° C. twenty milliliters of an ether solution containing 6.6 g (33 mmol) of p-methoxybenzyloxycarbonyl chloride was added while maintaining at 0° C, and the resulting mixture was stirred at 0° C. for 4 hours.

The dicyclohexylamine hydrochloride formed was separated by filtration. The filtrate was concentrated under reduced pressure, and the reaction product was crystallized by adding ethyl acetate to the concentrated solution to obtain 9.1 g of p-methoxybenzyl p-dimethyl-sulfoniophenyl carbonate methylsulfate (yield 70.7%).

Melting point: 106–108° C.
IR: 1750 cm−1 C=O).
1H-NMR (DMSO-d6):
$\delta = 3.27$, 6H(S)
3.37, 3H(S)
3.76, 3H(S)
5.22, 2H(S)
6.95, 7.40, 4H(each d,J=9.0 Hz)
7.61, 8.13, 4H(each d,J=9.0 Hz).
Elemental Analysis:
Calculated: C:50.22%, H:5.15%.
Found: C:49.73%, H:5.24%.

COMPARATIVE EXAMPLE 2

The reaction was carried out in the same manner as in Example 2 except that 3.0 g (30 mmol) of triethylamine was used in place of the dicyclohexylamine.

The amount of the desired p-methoxybenzyl p-dimethyl-sulfoniophenyl carbonate methylsulfate obtained was only 3.7 g (yield 28.7%), and a large amount of by-products was obtained.

COMPARATIVE EXAMPLE 3

The reaction was carried out in the same manner as in Example 2 except that 3.6 g (30 mmol) of N,N-dimethylaniline was used in place of the dicyclohexylamine.

The desired p-methoxybenzyl p-dimethylsulfoniophenyl carbonate methylsulfate could not be obtained at all.

EXAMPLE 3

Twenty eight point seven six grams (108 mmol) of p-dimethylsulfoniophenol methylsulfate was added to 750 ml of acetonitrile and stirred at room temperature for 30 minutes. Twenty seven point two zero grams (150 mmol) of dicyclohexylamine was dropped thereto, and the resulting mixture was stirred at room temperature for 1 hour and then cooled to 0° C. Twenty four point zero seven grams (120 mmol) of p-methoxy-benzyloxycarbonyl chloride was added while maintaining the temperature at 0° C., and the resulting mixture was stirred at 0° C. for 3 hours. The dicyclohexylamine hydrochloride formed was removed by filtration. The filtrate was concentrated by distilling the solvent, and the product was crystallized by adding ethyl acetate to the concentrated solution to obtain 33.10 g of p-methoxybenzyl p-dimethyl-sulfoniophenyl carbonate methylsulfate (yield 71.2%).

EXAMPLE 4

The reaction was carried out in the same manner as in Example 3 except that 16.98 g (150 mmol) of 2,6-dimethyl-piperidine was used in place of the dicyclohexylamine, and 700 ml of acetonitrile was used. The desired p-methoxybenzyl p-dimethylsulfoniophenyl carbonate methylsulfate was obtained in an amount of 23.87 g (yield 51.3%).

EXAMPLE 5

The reaction was carried out in the same manner as in Example 3 except that 15.18 g (150 mmol) of diisopropylamine was used in place of the dicyclohexylamine, and 400 ml of acetonitrile was used. The desired p-methoxybenzyl p-dimethylsulfoniophenyl carbonate methylsulfate was obtained in an amount of 19.15 g (yield 41.2%).

EXAMPLE 6

The reaction was carried out in the same manner as in Example 3 except that 19.39 g (150 mmol) of di-sec-butylamine was used in place of the dicyclohexylamine, and 700 ml of acetonitrile was used. The desired p-methoxybenzyl p-dimethylsulfoniophenyl carbonate methylsulfate was obtained in an amount of 17.04 g (yield 36.8%).

COMPARATIVE EXAMPLE 4

The reaction was carried out in the same manner as in Example 3 except that 16.07 g (150 mmol) of 2,6-lutidine was used in place of the dicyclohexylamine, and 300 ml of acetonitrile was used. Although 12.57 g of the desired p-methoxybenzyl p-dimethylsulfoniophenyl carbonate methylsulfate was obtained (yield 27.0%), a large amount of by-products was formed.

COMPARATIVE EXAMPLE 5

The reaction was carried out in the same manner as in Example 3 except that 25.00 g (119 mmol) of dicyclohexylethylamine was used in place of the dicyclohexylamine, and 700 ml of acetonitrile was used. The amount of the desired p-methoxybenzyl p-dimethylsulfoniophenyl carbonate methylsulfate formed was 6.87 g (yield 14.8%), and a large amount of by-products was formed.

EXAMPLE 7

Eight point zero grams (30 mmol) of p-dimethylsulfoniophenol methylsulfate was added to 200 ml of dried acetonitrile and stirred. 6.0 g (33 mmol) of dicyclohexylamine was dropped thereto, and the resulting mixture was stirred and then cooled to 0° C. Then 2.6 g (33 mmol) of acetyl chloride was added while maintaining at 0° C., and the resulting mixture was stirred at 5° C. for 4 hours.

The dicyclohexylamine hydrochloride formed was removed by filtration, and the filtrate was concentrated under reduced pressure. The product was crystallized by adding ether to the concentrated solution to obtain 8.7 g of 4-acetoxyphenyldimethylsulfonium methylsulfate (yield 94%).
Melting Point: 88–90° C.
IR: 1755 cm−1 (C=O)
1H-NMR (DMSO-d6):
δ=2.40, 3H(S)
3.30, 6H(S)
3.40, 8H(S)
7.45, 8.10, 4H(each d,J=8 Hz).
Elemental Analysis:
Calculated: C:42.84%, H:5.23%.
Found C:42.49%, H:5.12%.

EXAMPLE 8

In the same manner as in Example 7 except that 4.6 g (33 mmol) of benzoyl chloride was used in place of the acetyl chloride, 10.0 g of 4-benzoyloxyphenyldimethylsulfonium methylsulfate was obtained (yield 90%).
Melting Point: 173–175° C.
Elemental Analysis:
Calculated: C:51.88%, H:4.90%.
Found: C:51.84%, H:4.86%.

EXAMPLE 9

To 100 ml of acetonitrile were added 4.0 g (15 mmol) of p-dimethylsulfoniophenol methylsulfate and then 2.9 g (16 mmol) of dicyclohexylamine, which were stirred. One point nine grams (16 mmol) of valeryl chloride was added thereto and stirred at 25° C. for 2 hours.

The dicyclohexylamine hydrochloride formed was removed by filtration, and the filtrate was concentrated under reduced pressure.

The product was crystallized by adding ether to the concentrated solution to obtain 4.5 g of 4-valeryloxyphenyl-dimethylsulfonium methylsulfate. The yield, the melting point and the results of elemental analysis are shown in Table 1.

EXAMPLES 10 to 15

In the same manner as in Example 9 except that 16 mmol of each acid chloride shown in Table 1 was used in place of the valeryl chloride, 4-acyloxyphenyldimethylsulfonium methylsulfate corresponding to the acid chloride used was produced.

The yields, melting points and results of elemental analysis are shown in Table 1.

TABLE 1

| | | 4-Acyloxyphenyldimethylsulfonium Methylsulfate | | | |
|---|---|---|---|---|---|
| | | Yield | M.P. | Elemental Analysis (Calculated %/Found %) | |
| No. | Acid Chloride | (%) | (%) | C | H |
| Example 9 | Valeryl chloride | 86 | 89 to 91 | 47.98/47.86 | 6.33/6.32 |
| Example 10 | Hexanoyl chloride | 83 | 83 to 84 | 49.43/49.26 | 6.64/6.66 |
| Example 11 | Decanoyl chloride | 96 | 84 to 85 | 54.26/54.11 | 7.67/7.53 |
| Example 12 | Lauroyl chloride | 79 | 82 to 84 | 56.22/56.11 | 8.09/7.83 |
| Example 13 | Myristoyl chloride | 86 | 80 to 82 | 57.95/58.16 | 8.46/8.19 |
| Example 14 | Palmitoyl chloride | 80 | 77 to 79 | 59.49/59.12 | 8.79/8.76 |
| Example 15 | Stearoyl chloride | 92 | 84 to 87 | 60.87/60.38 | 9.08/9.05 |

EXAMPLE 16

To 200 ml of acetonitrile were added 8.0 g (30 mmol) of p-dimethylsulfoniophenol methylsulfate and then 6.0 g (33 mmol) of dicyclohexylamine, which were stirred. The reaction mixture was cooled to 5° C. and 5.7 g (33 mmol) of benzyloxycarbonyl chloride was added thereto. The resulting mixture was stirred at 5 to 10° C. for 1 hour.

The dicyclohexylamine hydrochloride formed was removed by filtration, and the filtrate was concentrated under reduced pressure. The product was crystallized by adding ethyl acetate to the concentrated solution to obtain 11.5 g of 4-(benzyloxycarbonyloxy)phenyldimethylsulfonium methylsulfate.

The yield, melting point and results of elemental analysis are shown in Table 2.

EXAMPLES 17 to 21

In the same manner as in Example 16 except that 30 mmol of each compound shown in Table 2 was used in place of the p-dimethylsulfoniophenol methylsulfate, a 4-(benzyloxy-carbonyloxy)phenyldimethylsulfonium salt corresponding to the salt used was obtained.

The yield, melting points and results of elemental analysis are shown in Table 2.

TABLE 2

| | | 4-(Benzyloxycarbonyloxy)-phenyldimethylsulfonium Salt | | | |
|---|---|---|---|---|---|
| | | Yield | M.P. | Elemental Analysis (Calculated %/Found %) | |
| No. | Anion | (%) | (°C.) | C | H |
| Example 16 | $CH_3SO_4^-$ | 96 | 106 to 108 | 50.99/51.14 | 5.03/5.12 |
| Example 17 | $Cl^-$ | 89 | 67 to 69 | 59.16/59.46 | 5.28/5.41 |
| Example 18 | $Br^-$ | 91 | 69 to 71 | 52.04/51.79 | 4.64/4.60 |
| Example 19 | $ClO_4^-$ | 79 | 141 to 143 | 49.42/49.82 | 4.41/4.28 |
| Example 20 | $p\text{-}CH_3\text{-}C_6H_4\text{-}SO_3^-$ | 86 | 155 to 157 | 59.98/60.19 | 5.25/5.16 |
| Example 21 | $HSO_4^-$ | about 75 | —* | 49.73/—* | 4.69/—* |

*Hygroscopic

EXAMPLE 22

In the same manner as in Example 16 except that 8.1 g (30 mmol) of 4-dimethylsulfonio-2-methylphenol perchlorate was used in place of the p-dimethylsulfoniophenyl methylsulfate, 11.1 g of benzyl-4-dimethylsulfonio-2methylphenyl carbonate perchlorate was obtained (yield 92%).
Melting point: 130–132° C.
Elemental Analysis:
Calculated: C:50.69%, H:4.75%.
Found: C:50.59%, H:4.73%.

EXAMPLE 23

Acylation in Aqueous Solution

Zero point eight three gram (5.03 mmol) of phenylalanine was added to 10 ml of water and 1.05 ml (7.53 mmol) of triethylamine was added. They were then dissolved by stirring at room temperature.

Two point six zero grams (6.04 mmol) of p-methoxybenzyl p-dimethylsulfoniophenyl carbonate methylsulfate (PMZ-DSP) obtained in Example 2 was added and stirred at room temperature for 15 hours. The resulting mixture was adjusted to pH 3 - 4 by adding a 2% aqueous HCl solution and then extracted twice with 70 ml of ethyl acetate. The extract was washed twice with 20 ml of water, dried over anhydrous sodium sulfate and then concentrated under reduced pressure. To the concentrated solution were added 30 ml of ether and then 1.9 g (4.5 mmol) of dicyclohexylamine (DCHA) to cause crystallization.

N-(p-methoxybenzyloxycarbonyl) phenylalanine dicyclohexylamine salt (PMZ-Phe-OH DCHA) as the desired product was obtained (yield: 1.94 g, 75.5%).

EXAMPLE 24

Twelve point tree four grams (46.3 mmol) of p-dimethylsulfoniophenol methylsulfate was dissolved in 180 ml of dried acetonitrile by stirring at room temperature for 30 minutes.

Ten point two milliliters (50.7 mmol) of dicyclohexylamine was added thereto. Upon ice cooling of the resulting mixture, a slurry-like mixture was obtained. To this mixture, a solution containing 13.20 g (51.0 mmol) of 9-fluorenyl-methoxycarbonyl chloride dissolved in 30 ml of acetonitrile was dropped with stirring. The time required for dropping was 30 minutes. The mixture was stirred at 0° C. for 2 hours and then a white solid of amine hydrochloride was separated by filtration.

This solid was further washed with 50 ml of acetonitrile. The filtrate obtained above and the acetonitrile used for the above washing were mixed and then the resulting mixture was concentrated by the use of an evaporator. The product was crystallized by adding ethyl acetate to the concentrated solution and then collected. The solid thus obtained was recrystallized from an acetonitrile solution containing ethyl acetate as a poor solvent to obtain the desired product of 9-fluorenylmethyl p-dimethyl-sulfoniophenyl carbonate methylsulfate. The purity of the desired product was determined by the high performance liquid chromatographic method and the NMR method.
Yield: 21.70 g (44.4 mmol, 95.8).
Purity: 99.3%.
Melting Point: 117–122° C.
IR: 1760 cm−1 (C=0).
1H-NMR(CDCl3), δ=3.42 (6H, s). 3.65 (3H, s), 4.16 to 4.62 (3H, m), 7.16 to 8.20 (12H, m).

EXAMPLE 25

The procedure of Example 24 was repeated with the exception that 2,6-dimethylpiperidine was used in place of the dicyclohexylamine.
Yield: 20.40 g (41.8 mmol, 90.8%).
Purity: 99.0%.

EXAMPLE 26

The procedure of Example 24 was repeated with the exception that diisopropylamine was used in place of the dicyclohexylamine.
Yield: 18.13 g (37.1 mmol, 80.1%).
Purity: 98.2%.

COMPARATIVE EXAMPLE 26

The procedure of Example 24 was repeated with the exception that triethylamine was used in place of the dicyclohexylamine.
Yield: 9.95 g (20.4 mmol, 44.1%).
Purity: 84.1%.

EXAMPLE 27

Acylation in Aqueous Solution

Zero point three eight zero gram (5.06 mmol) of glycine was added to 13.5 ml of a 10% aqueous sodium carbonate solution and dissolved by stirring at room temperature.

Two point nine five grams (6.04 mmol) of 9-fluorenylmethyl-p-d-dimethylsulfoniophenyl carbonate methylsulfate obtained in Example 24 as dissolved in 13.5 ml of water was dropped while cooling with ice, and stirred at room temperature for 3 hours.

The reaction mixture was diluted with 500 ml of water and washed twice with 75 ml of ether. The pH was adjusted to 1 or 2 by adding concentrated hydrochloric acid to the aqueous layer while cooling in an ice bath, and extraction was carried out three times with 150 ml of ethyl acetate. The combined orgainic layer was washed with 100 ml of water and dried over anhydrous magnesium sulfate. After removal of the drying agent, the solvent was distilled away from the filtrate under reduced pressure. The product was crystallized by adding ether to obtain N-(9-fluorenyl-methoxycarbonyl) glycine.

Yield: 1.45 g (4.88 mmol, 96.4%).

What is claimed is:

1. A process for producing a sulfonium compound of the formula

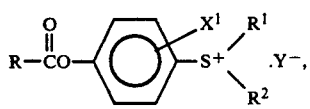

which process comprises reacting a p-dialkylsulfoniophenol of the formula

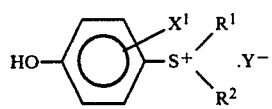

and a carbonyl halogenide compound of the formula

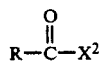

in the presence of a secondary amine having a structure in which two secondary alykl groups are linked to the nitrogen atom:
wherein R1 and R2 are the same or different and are independently an alkyl group having 1 to 4 carbon atoms, X1 is a hydrogen atom, a halogen atom or an alkyl group having 1 to 4 carbon atoms, Y is a halogen anion, a perchlorate anion, an alkylsulfate anion, a hydrogensulfate anion or a p-toluenesulfonate anion, R is an alkyl group having 1 to 20 carbon atoms, a tert-butoxty group, a benzyloxy group, a p-methoxybenzyloxy group, a phenyl group or a 9-fluorenylmethoxy group, and X2 is a halogen atom,
   wherein the reacting is carried out in a solvent selected from the group consisting of polar aprotic solvents, ethers and halogenated hydrocarbons, at a temperature of −80° C. to 30+ C. and for a reaction time of 0.5 hour to 10 hours.

2. The process as claimed in claim 1 wherein the secondary amine having the structure in which two secondary alkyl groups are linked to the nitrogen atom is at least one amine selected from the group consisting of dicyclohexylamine, diisopropylamine, di-sec-butylamine and 2,6-dimethylpiperidine.

3. The process as claimed in claim 1 wherein the secondary amine having the structure in which two secondary alkyl groups are linked to the nitrogen atom is used in an amount of 0.5 to 2.0 mol per mol of the p-dialykysulfoniophenol represented by the formula (I).

4. The process as claimed in claim 1 wherein the carbonyl halogenide compound represented by the formula (II) is used in an amount of 0.5 to 2.0 mol per mol of the p-dialkylsulfoniophenol represented by the formula (I).

5. The process as claimed in claim 1 wherein R1 and R2 of the formulae (I) and (III) are methyl groups or ethyl groups.

6. The process as claimed in claim 1 wherein Y− of the formulae (I) and (III) is an alkylsulfate anion or a hydrogensulfate anion.

7. The process as claimed in claim 1 wherein R of the formulae (II) and (III) is a tert-butoxy group, a benzyloxy group, a p-metoxybenzyloxy group or a 9-fluorenylmethoxy group.

8. The process as claimed in claim 1, wherein R1 and R2 are the same or different and are selected from the group consisting of a methyl group and ethyl group; X2 is a halogen atom selected from the group consisting of fluorine, chlorine and bromine; Y− is an anion selected from the group consisting of an alkylsulfate anion and a hydrogensulfate anion and X1 is selected from the group consisting of a hydrogen atom, an alkyl group having 1 to 4 carbon atoms and a halogen atom selected from the group consisting of fluorine, chlorine and bromine.

9. The process as claimed in claim 1, wherein the carbonyl halogenide compound is selected from the group consisting of acetyl fluoride, acetyl chloride, propionyl chloride, propionyl bromide, butyryl chloride, valeryl chloride, hexanoyl chloride, octanoyl chloride, decanoyl chloride, lauroyl chloride, myristoyl chloride, palmitoyl chloride, stearoyl chloride, tert-butoxycarbonyl chloride, benzyloxycarbonyl chloride, tert-butoxycarbonyl chloride, benzyloxycarbonyl chloride, p-methoxybenzylcarbonyl chloride, 9-fluorenylmethoxycarbonyl chloride, benzoyl chloride and benzoyl bromide.

10. The process as claimed in claim 9 wherein the secondary amine having the structure in which two secondary alkyl groups are linked to the nitrogen atom is used in an amount of 0.8 to 1.5 mol per mol of the p-dialkylsulfoniophenol of the formula (I), the carbonyl halogenide compound is used in amount of 0.8 to 1.5 mol per mol of the p-dialkylsulfoniophenol of the formula (I) and the reaction temperature is −30 to =10° C.

11. The process of claim 10, wherein the solvent is selected from the group consisting of acetonitrile, diethyl ether, tetrahydrofuran and dicloromethane.

12. The process as claimed in claim 1, wherein the carbonyl halogenide is 9-fluorenylmethoxycarbonyl chloride and the reaction is conducted for 0.5 to 4 hours at a temperature of −20° C. to =30° C.

13. The process as claimed in claim 2, wherein the secondary amine having the structure in which two secondary alkyl groups are linked to the nitrogen atom is used in an amount of 0.5 to 2.0 mol per mol of the p-dialkysulfoniophenol of the formula (I) and the carbonyl halogenide compound of the formula (II) is used in an amount of 0.5 to 2.0 mol per mol of the p-dialkysulfonionphenol represented by the formula (I).

14. The process as claimed in claim 11, wherein the carbonyl chloride compound having the formula RCOCl is used in an amount of 0.5 to 2.0 mol per mol of the p-dimethyl-sulfoniophenol methylsulfate and the reaction is conducted at −80° C. to +30° C. for 0.5 hours to 10 hours.

15. The process as claimed in claim 1, wherein R is a tert-butoxy group.

16. The process as claimed in claim 1, wherein R is a benzyloxy group.

17. The process as claimed in claim 1, wherein R is a p-methoxylbenzyloxy group.

18. The process as claimed in claim 1, wherein R is a 9-fluorenylmethoxy group.

19. The process as claimed in claim 1, wherein the p-dialkylsulfoniophenol is p-dimethylsulfoniophenol methyl sulfate, the carbonyl halogenide is benzyloxycarbonylchloride, the secondary amine is dicyclohexylamine and the solvent is acetonitrile.

20. The process as claimed in claim 1, wherein the p-dialkylsulfoniophenol is p-dimethylsulfoniophenol methyl sulfate, the carbonyl halogenide is benzyloxycarbonylchloride, the secondary amine is 2,6-dimethylpiperidine and the solvent is acetonitrile.

21. The process as claimed in claim 1, wherein the p-dialkylsulfoniophenol is p-dimethylsulfoniophenol methyl sulfate, the carbonyl halogenide is benzyloxycarbonylchloride, the secondary amine is diisopropylamine and the solvent is acetonitrile.

22. The process as claimed in claim 1, wherein the p-dialkylsulfoniophenol is p-dimethylsulfoniophenol methyl sulfate, the carbonyl halogenide is benzyloxycarbonylchloride, the secondary amine is di-sec-butylamine and the solvent is acetonitrile.

23. A process for producing a sulfonium compound of the formula (III')

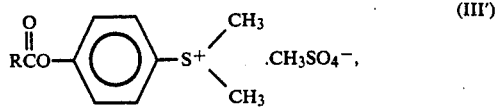

wherein R is a tert-butoxy group, a benzyloxy group, a p-methoxybenzyloxy group, a phenyl group or a 9-fluorenylmethoxy group, which process comprises reacting p-dimethylsulfoniophenol methylsulfate having the formula

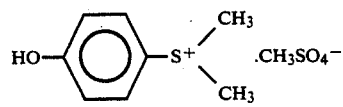

and a carbonyl chloride compound of the formula R-COCl in an acetonitrile solvent in the presence of at least one amine selected from the group consisting of dicyclohexylamine, diisopropylamine, di-sec-butylamine and 2,6-dimethylpiperidine 24. The process as claimed in claim 23 wherein the amine is used in an amount of 0.5 to 2.0 mol per mol of the p-dimethylsulfoniophenol methylsulfate.

25. The process as claimed in claim 23 wherein the carbonyl chloride compound having the formula: RCOCl is used in an amount of 0.5 to 2.0 mol per mol of the p-dimethylsulfoniophenol methylsulfate.

26. The process as claimed in claim 23 wherein the reaction is at a temperature of −80° C. to 30° C. and the reaction time is from 0.5 hour to 10 hours.

* * * * *